United States Patent
Farooqui (10) Patent No.: US 8,117,694 B2
(45) Date of Patent: *Feb. 21, 2012

(54) TABLE DRIVE SYSTEM

(75) Inventor: Asghar Ali Farooqui, Karnataka (IN)

(73) Assignee: General Electric Company, Schenectady, NY (US)

( * ) Notice: Subject to any disclaimer, the term of this patent is extended or adjusted under 35 U.S.C. 154(b) by 16 days.

This patent is subject to a terminal disclaimer.

(21) Appl. No.: 12/349,554

(22) Filed: Jan. 7, 2009

(65) Prior Publication Data

US 2009/0172882 A1 Jul. 9, 2009

(30) Foreign Application Priority Data

Jan. 8, 2008 (IN) ................................ 65/CHE/2008

(51) Int. Cl.
  *A61G 13/04* (2006.01)
  *B65G 47/34* (2006.01)
(52) U.S. Cl. ................. 5/601; 5/943; 5/610; 198/468.9; 384/45
(58) Field of Classification Search .............. 5/601, 611, 5/610, 607, 943; 74/27; 384/45; 198/468.9
See application file for complete search history.

(56) References Cited

U.S. PATENT DOCUMENTS

| | | | |
|---|---|---|---|
| 6,712,512 B2* | 3/2004 | Teramach et al. | 384/45 |
| 7,552,490 B2* | 6/2009 | Saracen et al. | 5/601 |
| 2009/0252301 A1* | 10/2009 | Saracen et al. | 5/611 |

* cited by examiner

*Primary Examiner* — Robert G Santos
*Assistant Examiner* — Brittany Wilson
(74) *Attorney, Agent, or Firm* — Global Patent Operation; Jonathan E. Thomas (57) ABSTRACT

A table drive system comprising a first drive assembly configured for moving a support table in a first direction, a second drive assembly configured for moving the support table in a second direction, a third drive assembly configured for moving the support table in a third direction and a first drive motor coupled to the first drive assembly, the second drive assembly and the third drive assembly is provided. The first drive motor is configured to drive the first drive assembly, the second drive assembly and the third drive assembly.

22 Claims, 11 Drawing Sheets

FIG. 1

Patient positioning system
120

Patient support table
125

First drive assembly
205

Second drive assembly
210

Third drive assembly
215

First drive motor
220

TABLE DRIVE SYSTEM

FIELD OF INVENTION

This invention relates generally to a table drive system and more particularly to a drive system for moving a table in multiple directions.

BACKGROUND OF THE INVENTION

Patient positioning systems engage and support a medical subject undergoing a medical procedure such as a diagnostic procedure, a therapeutic procedure and a surgical procedure. Typically a patient positioning system comprises a support table on which the medical subject is positioned and a drive system for positioning the support table. The process of aligning the medical subject for the medical procedure involves motion of the support table along multiple axes. Therefore, the drive system configured for positioning the support table is desired to be capable of moving the support table along multiple axes.

For moving the support table along multiple axes, the drive system can comprise a plurality of drive assemblies. Each drive assembly can be configured to drive the motion of the support table along a single axis.

Conventional methodology of achieving motion of the support table along multiple axes comprises driving each axis by an independent drive motor. Thus the patient positioning system conventionally comprises multiple drive motors as each drive assembly is coupled to a single drive motor in a very complex and inaccessible compact way. The drive motors are expensive and hence using a plurality of independent drive motors may not be an economical option. Moreover, using a plurality of independent drive motors requires sufficient space to facilitate appropriate assembly, maintenance and repair. Another drawback of using multiple drive motors is that the capacity of each drive motor is often underutilized in terms of functioning and idle time.

Hence, there exists a need to provide a simple, compact, reliable, serviceable and cost effective drive system for a patient positioning system.

SUMMARY OF THE INVENTION

The above-mentioned shortcomings, disadvantages and problems are addressed herein which will be understood by reading and understanding the following specification.

In an embodiment, a table drive system is provided. The table drive system comprises a first drive assembly configured for moving a support table in a first direction, a second drive assembly configured for moving the support table in a second direction, a third drive assembly configured for moving the support table in a third direction and a first drive motor coupled to the first drive assembly, the second drive assembly and the third drive assembly. The first drive motor is configured to drive the first drive assembly, the second drive assembly and the third drive assembly.

In another embodiment, a drive system for a patient positioning system is provided. The drive system comprises at least three driving members configured for moving a patient support table and a first drive motor coupled to the at least three driving members. The first drive motor is configured to drive the at least three driving members.

In yet another embodiment, a patient positioning system is provided. The patient positioning system comprises a patient support table, a first drive assembly adapted for moving the patient support table in a first direction, a second drive assembly adapted for moving the patient support table in a second direction, a third drive assembly configured for moving a support table in a third direction and a first drive motor coupled to the first drive assembly, the second drive assembly and the third drive assembly. The first drive motor is configured to drive the first drive assembly, the second drive assembly and the third drive assembly.

Systems and methods of varying scope are described herein. In addition to the aspects and advantages described in this summary, further aspects and advantages will become apparent by reference to the drawings and with reference to the detailed description that follows.

DETAILED DESCRIPTION OF THE INVENTION

In the following detailed description, reference is made to the accompanying drawings that form a part hereof, and in which is shown by way of illustration specific embodiments, which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

Figure 1:
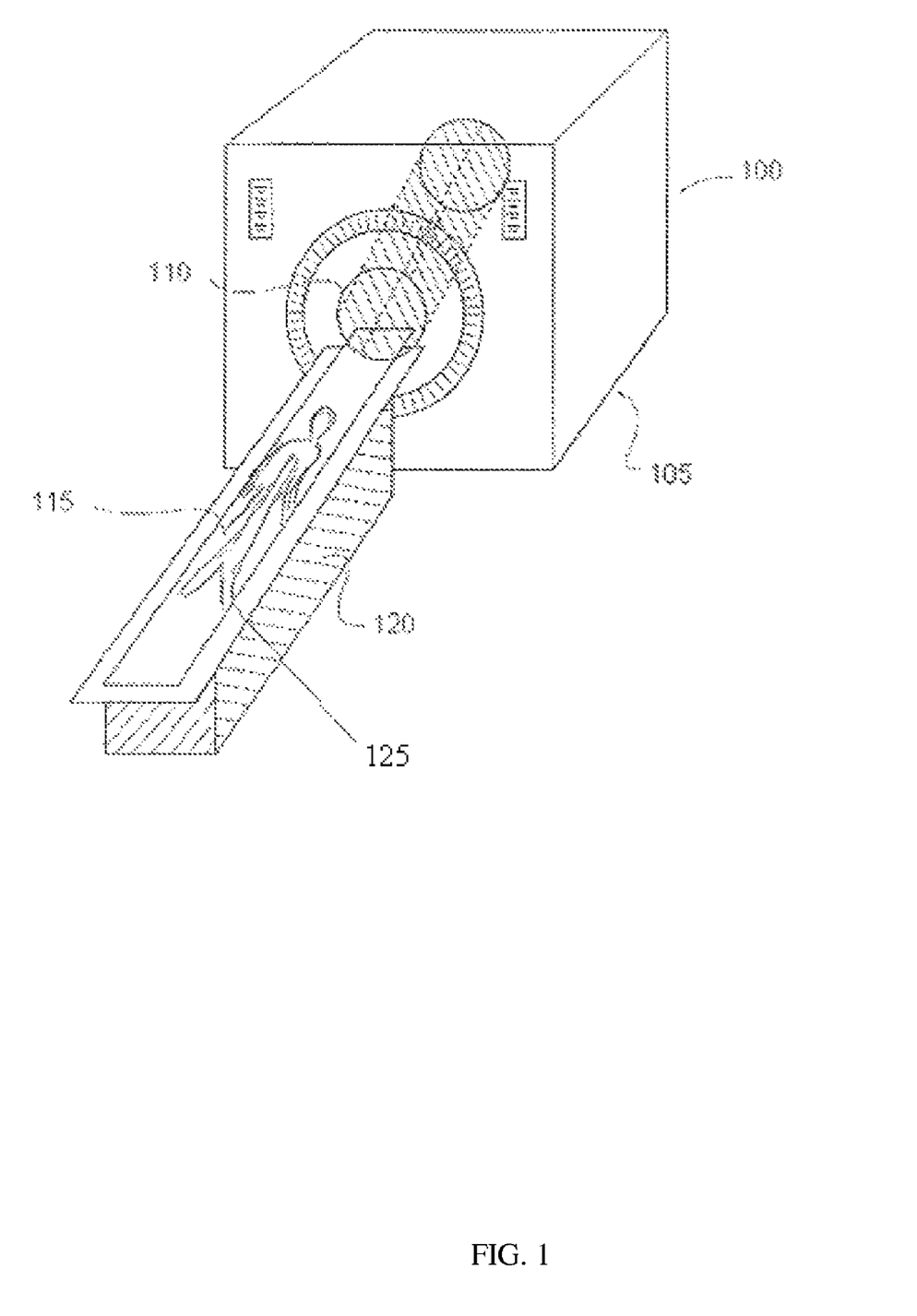
FIG. 1 shows a schematic diagram of an example of an imaging device in an embodiment of the invention.

FIG. 1 shows a schematic diagram of an example of an imaging device 100. The imaging device 100 can be one of a computed tomography device, a positron emission tomography device, a magnetic resonance imaging device, an ultrasound-imaging device, an x ray device, or a combination of such devices. One skilled in the art will however appreciate that, the examples of the imaging device 100 are not limited to the examples mentioned above and the invention shall have full scope of the claims.

The imaging device 100 comprises an imaging gantry 105 that includes a bore or tunnel 110 for receiving a medical subject 115. The medical subject 115 refers to an article, a person or an animal. In one embodiment, as shown in FIG. 1, a patient positioning system 120 for positioning the medical subject 115 in the imaging gantry 105 is provided. The patient positioning system 120 comprises a patient support table 125 for supporting and engaging the medical subject 115. The patient support table 125 can be configured to be displaced to multiple positions along multiple axes to facilitate the positioning of the medical subject 115 for imaging. In one embodiment, the patient support table 125 is configured to displace the medical subject 115 along longitudinal, lateral, rotational, vertical and tilt directions (which may be referred to as the X, Y, R, Z or A-axis directions).

Skilled artisans shall however appreciate that the patient positioning system 120 forming a part of the imaging device 100 is an exemplary embodiment and in general the patient positioning system 120 can be a part of a diagnostic device such as an imaging device 100, a therapeutic device and a surgical device. Further, the patient positioning system 120 can be either integral with or separate from the imaging gantry 105 in the imaging device 100.

Figure 2:
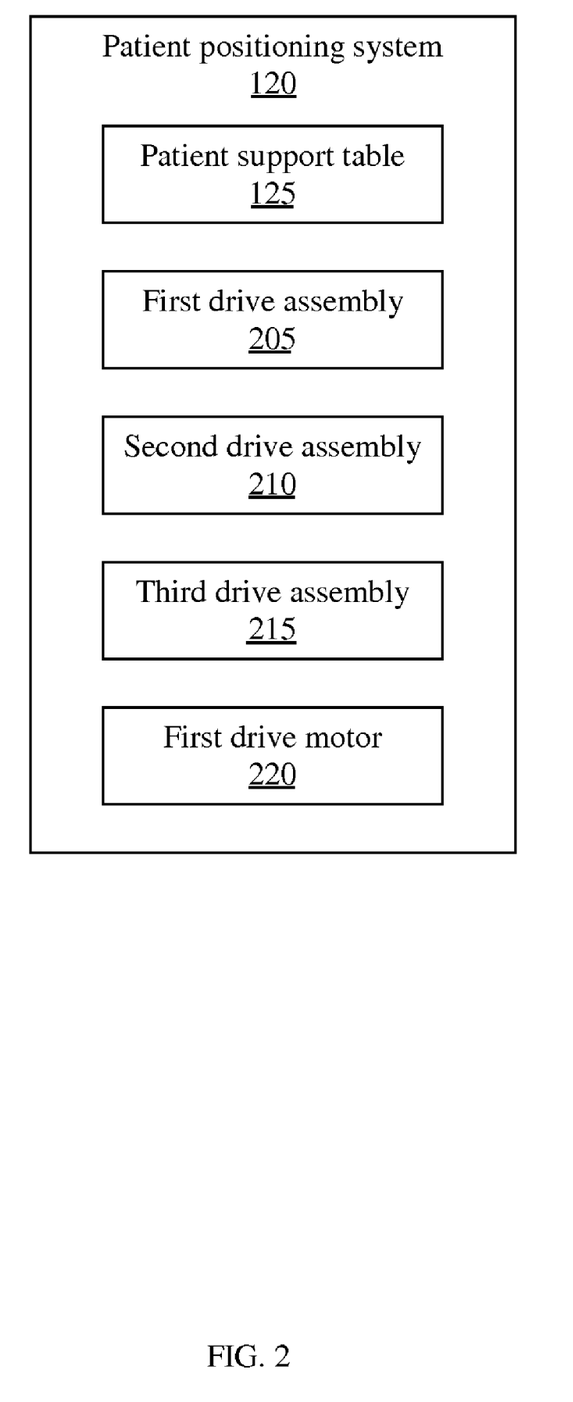
FIG. 2 shows a block diagram of an example of a patient positioning system in an embodiment of the invention.

FIG. 2 depicts a block diagram of the patient positioning system 120 in one embodiment of the invention. The patient positioning system 120 comprises the patient support table 125, a combination of a first drive assembly 205, a second drive assembly 210 and a third drive assembly 215, each configured to drive the patient support table 125, and a first drive motor 220 coupled to the first drive assembly 205, the second drive assembly 210 and the third drive assembly 215, the first drive motor 220 being configured to drive the first drive assembly 205, the second drive assembly 210 and the third drive assembly 215 to move the patient support table 125 in multiple directions. In this embodiment, a single drive motor (i.e., 220) is advantageously used to drive three different drive assemblies (i.e., 205, 210 and 215).

Figure 3:
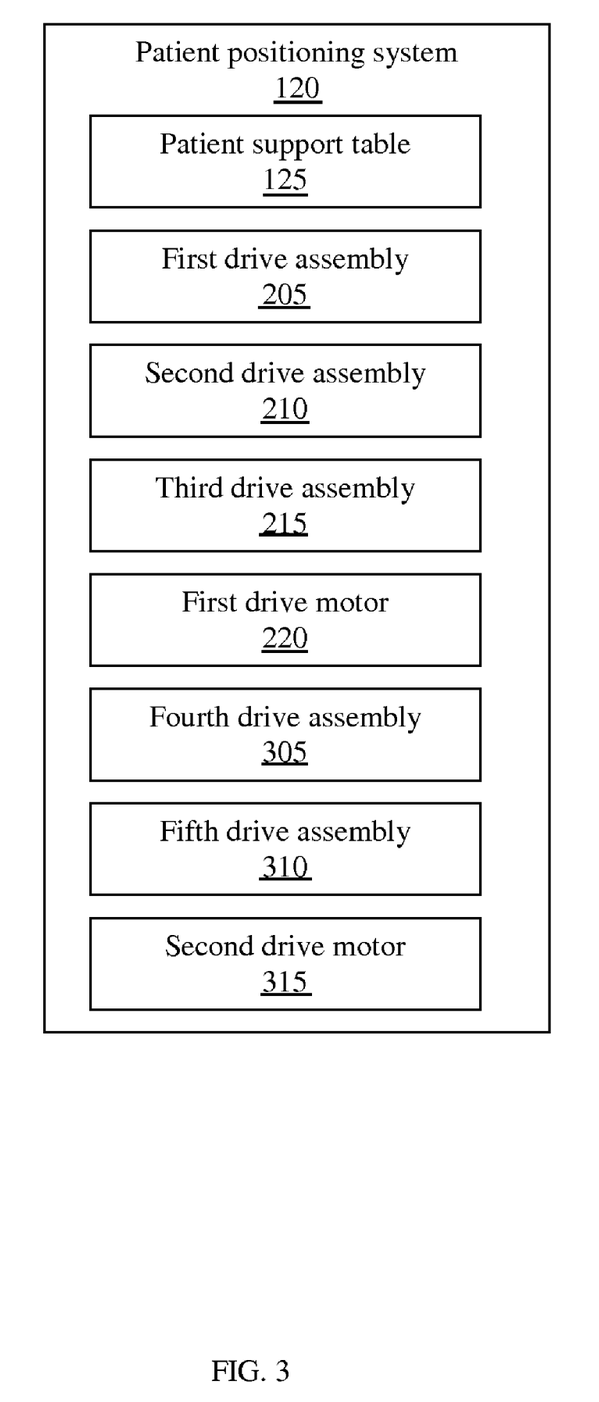
FIG. 3 shows a block diagram of an example of a patient positioning system in another embodiment of the invention.

In another embodiment as shown in FIG. 3, the patient positioning system 120 can further comprise a fourth drive assembly 305 and a fifth drive assembly 310 in combination with the first drive assembly 205, the second drive assembly 210 and the third drive assembly 215, and a second drive motor 315 can be configured to drive the fourth drive assembly 305 and the fifth drive assembly 310. In this embodiment, two drive motors (i.e., 220 and 315) can be advantageously used to drive five different drive assemblies (i.e., 205, 210, 215, 305 and 310). Skilled artisans shall however appreciate that the number of the drive assemblies in the patient positioning system 120 is not limited and the patient positioning system 120 can comprise a plurality of drive assemblies as claimed in the invention.

The multiple drive assemblies 205, 210, 215, 305 and 310 of the patient positioning system 120 can be configured to drive the patient support table 125 along multiple axes. For example, the first drive assembly 205 can be configured to drive the patient support table 125 in a first direction such as a longitudinal or X direction, the second drive assembly 210 can be configured to drive the patient support table 125 in a second direction such as a lateral or Y direction, the third drive assembly 215 can be configured to drive the patient support table 125 in a third direction such as a rotational or R direction, the fourth drive assembly 305 can be configured to drive the patient support table 125 in a fourth direction such as a vertical or Z direction and the fifth drive assembly 215 can be configured to drive the patient support table 125 in a fifth direction such as a tilt or A direction. An electronic control module may be provided for selectively energizing the respective drive assemblies 205, 210, 215, 305 and 310.

Based on operator input, the electronic control module or other switch arrangement can be configured to control which drive assembly 205, 210, 215, 305 or 310 is energized.

In one embodiment, each of drive assemblies 205, 210 and 215 is driven only when the other two of drive assemblies 205, 210 and 215 are not driven, thereby limiting the driving requirements needed from the first drive motor 220. In contrast, each of drive assemblies 305 and 310 may be driven together or separately depending on the direction of the motion required.

Each of the first drive motor 220 and the second drive motor 315 configured to drive multiple drive assemblies 205, 210, 215, 305 and 310 can be a double-end shaft motor comprising shafts that extend outwardly in opposite directions. Depending on the requirement, the first drive motor 220 and the second drive motor 315 can be one of a stepper, servo and a geared motor driven by AC/DC power. Further, the first drive motor 220 can be selected to be rated with maximum torque output. The first drive motor 220 with the maximum torque output is capable of moving the patient support table 125 independently along each of the multiple axes. Further, the motion of the patient support table 125 along each axis can be independently controlled with the help of a computer program.

Figure 4:
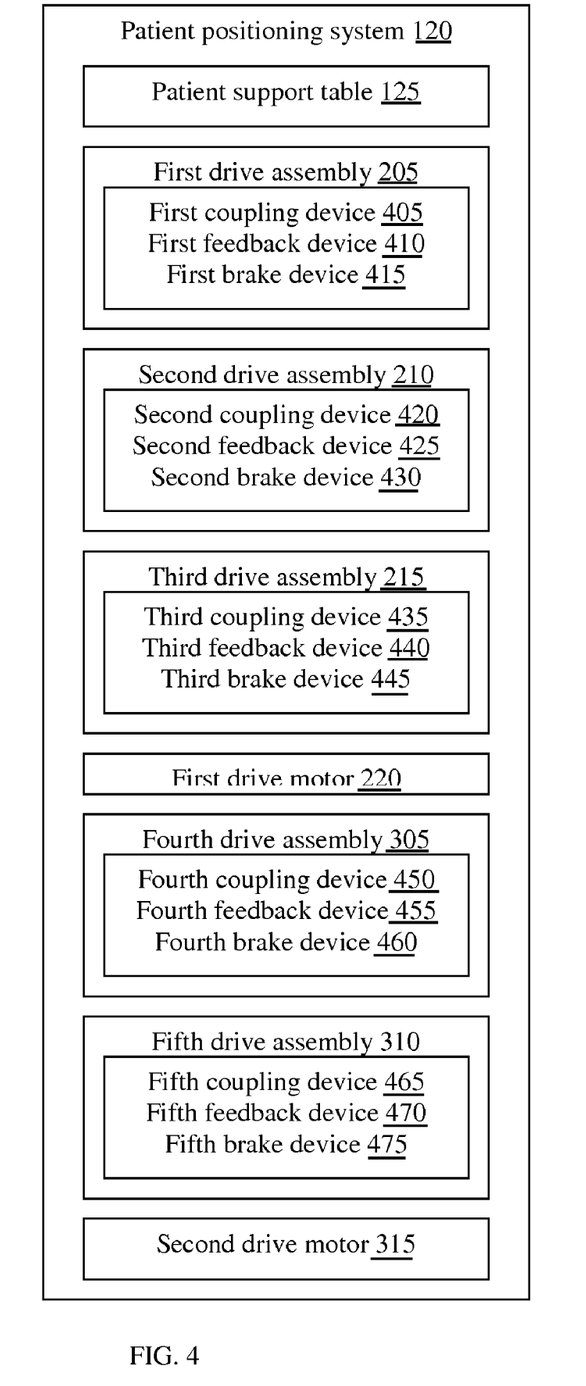
FIG. 4 shows a block diagram of an example of a patient positioning system in yet another embodiment of the invention.

Turning now to FIG. 4, each of the first drive assembly 205, the second drive assembly 210 and the third drive assembly 215 can be coupled to the first drive motor 220 using a coupling device and each of the fourth drive assembly 305 and the fifth drive assembly 310 can be coupled to the second drive motor 315 using a coupling device. The coupling device can be generally used in the patient positioning system 120 as a safety device. In the patient positioning system 120 provided in one embodiment, the coupling device can be used for transmission in addition to being used as the safety device. Further, the coupling device when clubbed with a drive assembly provides smooth engagement and eliminates chatter.

Further, each drive assembly 205, 210, 215, 305 and 310 can be directly coupled to a feedback device at a first end and a brake device at a second end. The feedback device provides a greater positioning accuracy whereas the brake device provides safety and imparts a robust design feature to the drive assembly. Accordingly, the first drive assembly 205 comprises a first coupling device 405, a first feedback device 410 and a first brake device 415, the second drive assembly 210 comprises a second coupling device 420, a second feedback device 425 and a second brake device 430, the third drive assembly 215 comprises a third coupling device 435, a third feedback device 440 and a third brake device 445, the fourth drive assembly 305 comprises a fourth coupling device 450, a fourth feedback device 455 and a fourth brake device 460 and the fifth drive assembly 305 comprises a fifth coupling device 465, a fifth feedback device 470 and a fifth brake device 475.

The coupling devices 405, 420, 435, 450 and 465 can be employed to selectively engage multiple drive assemblies 205, 210, 215, 305 and 310 coupled to one of the first drive motor 220 and the second drive motor 315, to drive the motion of the patient support table 125 along multiple axes. At a given time, a single coupling device can be actuated to activate the associated drive assembly thereby moving the patient support table 125 along a predetermined axis. During the time when one of the coupling devices (e.g., 405), is engaged with the first drive motor 220, the rest of the coupling devices (e.g., 420 and 435) can be disengaged. However, when the patient support table 125 is been driven along one axis, the disengaged coupling devices (e.g., 420 and 435) may be ideally rotating without transmission. Further, in one exemplary embodiment, each coupling device 405, 420, 435, 450 and 465 can be selected to be an electro-mechanical clutch.

The revolution-per-minute (RPM) of the first drive motor 220 and the second drive motor 315 is in close loop with the corresponding drive assembly 205, 210, 215, 305 or 310 through the feedback device 410, 425, 440, 455 or 470. The feedback device 410, 425, 440, 455 or 470 can be an absolute encoder for providing an indication of an absolute position of the patient support table 125.

The brake device 415, 430, 445, 460 or 475 coupled at another end of each drive assembly 205, 210, 215, 305 and 310 can be configured to bring in redundancy into the patient positioning system 120. Each brake device 415, 430, 445, 460 or 475 coupled to a single drive assembly 205, 210, 215, 305 or 310 can be located to control the motion of the patient support table 125 along a single axis. Each brake device 415, 430, 445, 460 or 475 can be configured to lock the motion of the patient support table 125 at a predetermined position on a selected axis during the time when the motion of the patient support table 125 is initiated in another axis or when the transmission system is engaged with the motion of the patient support table 125 along other axis. In an exemplary embodiment, each brake device 415, 430, 445, 460 or 475 can be selected to be an electro magnetic brake.

Figure 5:
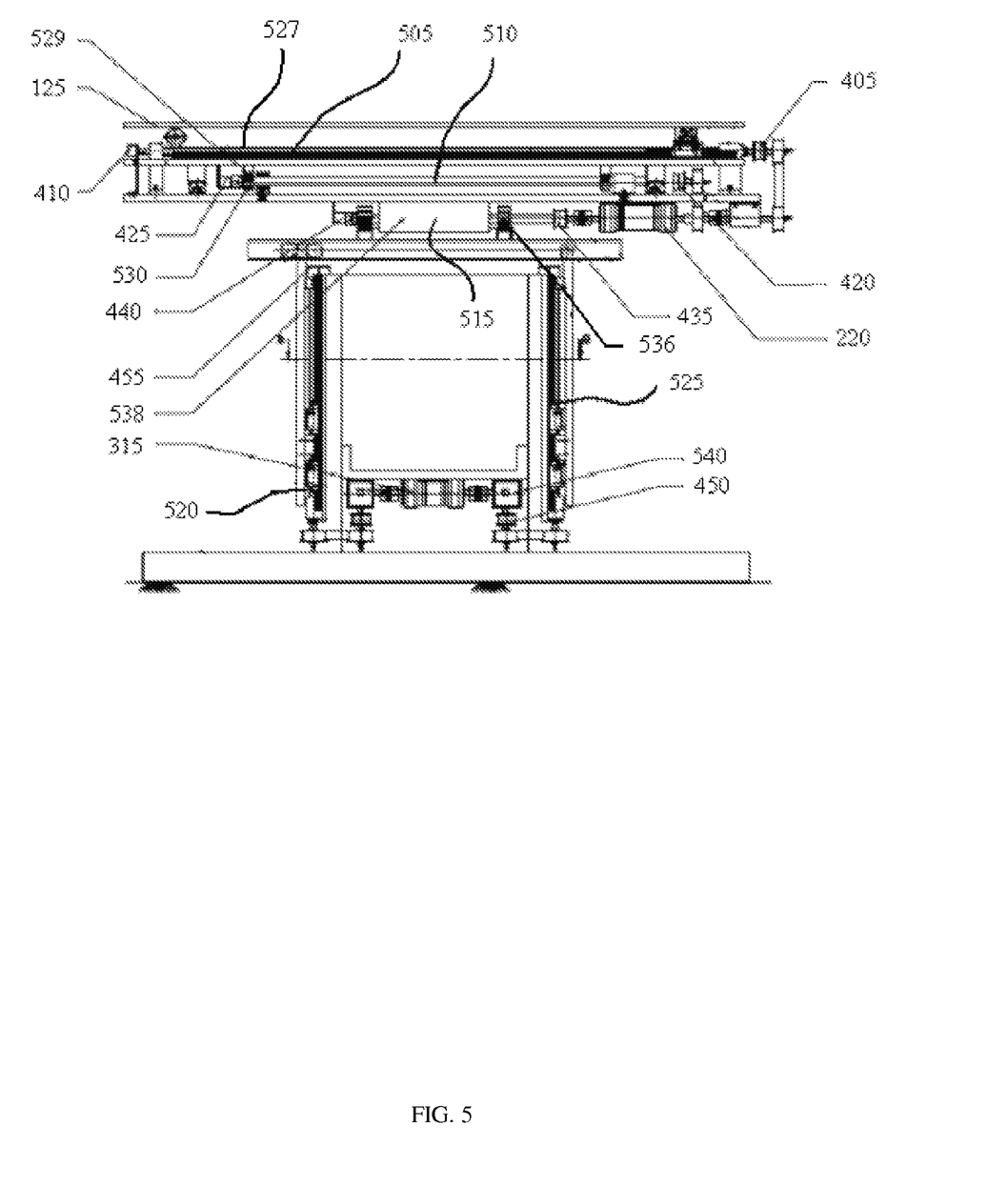
FIG. 5 shows a schematic diagram of an exemplary embodiment of the patient positioning system comprising a double-ended shaft motor coupled to three drive assemblies in one embodiment of the invention.
Figure 6:
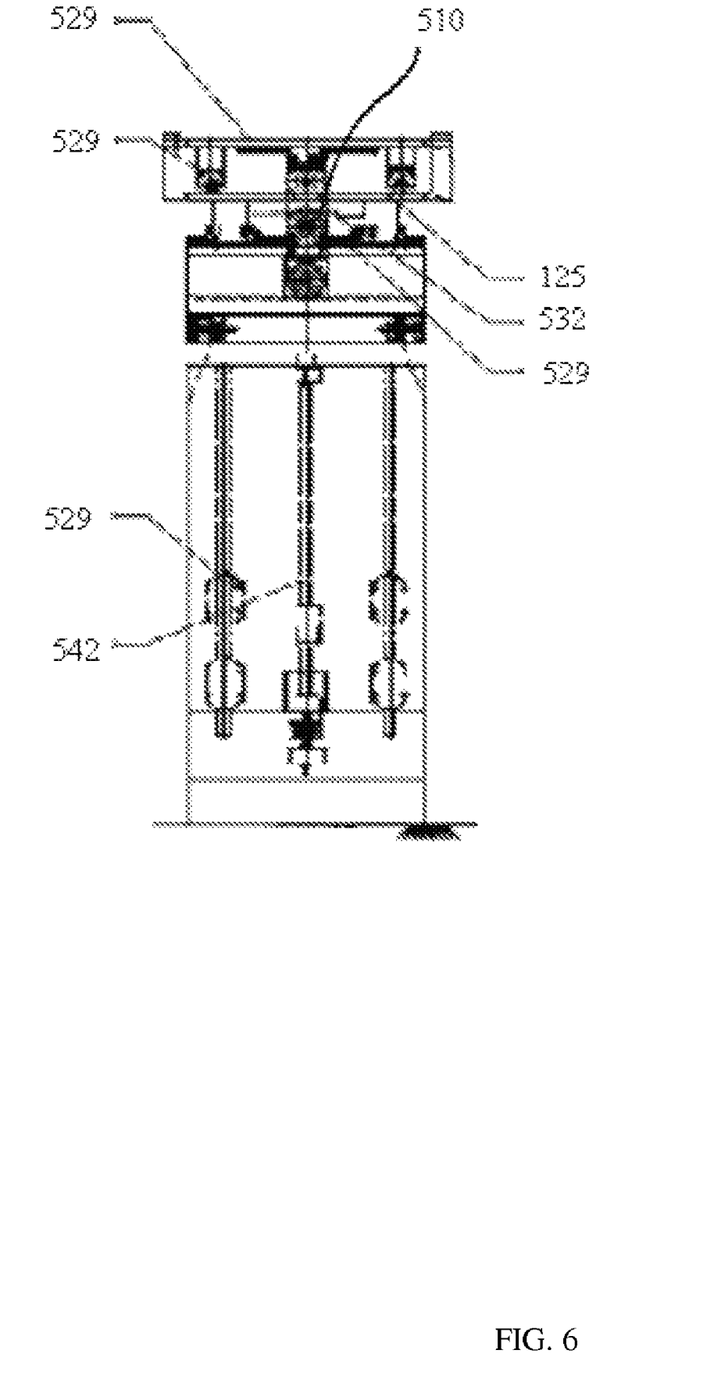
FIG. 6 shows a schematic diagram of the side view of the exemplary embodiment of the patient positioning system shown in FIG. 5.

FIG. 5 and FIG. 6 show the front view and the side view of the patient positioning system 120 depicting the coupling between the first drive motor 220 and the three drive assemblies 205, 210 and 215, as well as the coupling between the second drive motor 315 and the two drive assemblies 305 and 310. The first drive assembly 205, the second drive assembly 210 and the third drive assembly 305 can be mounted on a common mounting member (not shown) using a fixture such as, a support bracket, fastened or welded on to the mounting member (not shown). The mounting member (not shown) can be a longitudinal plate for example.

In one exemplary embodiment, the first drive assembly 205, the fourth drive assembly and the fifth drive assembly may each comprise a screw drive assembly 505, 520 and 525 respectively, the second drive assembly 210 may comprise a rack and pinion drive assembly 510 and the third drive assembly 305 may comprise a gearbox drive assembly 515. One skilled in the art shall however appreciate that the first drive assembly 205, the second drive assembly 210, the third drive assembly 215, the fourth drive assembly 305 and the fifth drive assembly 310 are not limited by the examples given above and each drive assembly 205, 210, 215, 305 and 310 can be substituted by more viable options.

The screw drive assembly 505 comprises a driving screw 527 and one or more linear motion guides 529. Typically, linear motion guides 529 are linear motion bearings that bear loads to guide the linear motion. The linear motion guide 529 facilitates the driving screw 527 to be in a predetermined position when the patient support table 125 moves along the second direction. Thus, the presence of the linear motion guide 529 adjacent to the driving screw 527 facilitates the motion of the patient support table 125 along the second direction.

The motion of the patient support table 125 along the second direction can be achieved by using a transmission comprising a rack and pinion arrangement. The rack and pinion drive assembly 510 comprises at least one pinion 530 engaged with a rack 532 for transmitting the motion from the first drive motor 220 to the patient support table 125 for effecting lateral movement of the patient support table 125.

The at least one pinion 530 is rotatably mounted at the center in the widthwise direction of the patient support table 125 with the rotating axis of the pinion 530 extending horizontally and perpendicularly to the lateral direction of the patient support table 125. The rack 532 movably coupled to the pinion 530 is fixedly mounted at the center in the widthwise direction of the patient support table 125 as extending in the lateral direction of the patient support table 125.

Further, the motion of the patient support table 125 along the third direction can be achieved by using a continuous circular rack and pinion arrangement 515. The third drive assembly 215 is mounted and connected by a robust gear and bearing sub-assembly 536. The two pinions running on the circular rack are configured to rotate in opposite direction to each other. The third drive assembly 215 further comprises a thrust bearing assembly 538 that can be anchored to a rotating part on its axis.

The motion of the patient support table 125 along the fourth direction can be achieved by actuating the two coupling devices 450 and 465. The patient support table 125 is moved in the vertical direction with the help of two ball screws 520 and 525 driven with a double end shaft motor, i.e., the second drive motor 315, through a gearbox 540. A rigid structure with two pairs of linear motion guides 529 driven by a ball screw 542 facilitates this motion. The two ball screws 520 and 525 are identical and can be driven by a single motor i.e., the second drive motor 315 through an approximately identical pair of gearboxes and transmission accessories. The patient support table 125 moves vertically, parallel to the ground, when both the screw drive assemblies 520 and 525 are engaged. Thus, the motion of the patient support table 125 in the fourth direction is achieved by engaging both the coupling devices 450 and 465, as this is a built in feature of this design.

Figure 7:
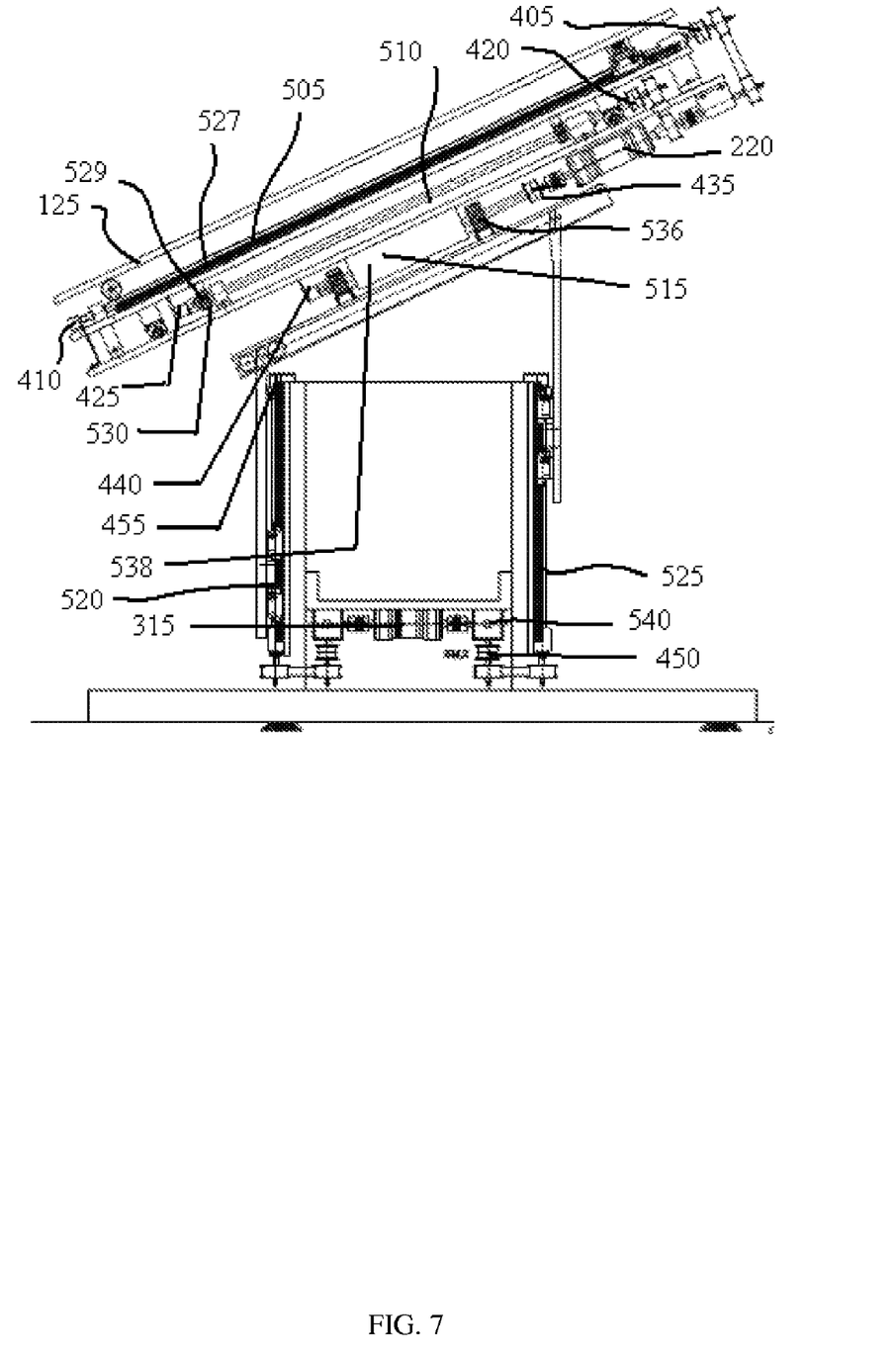
FIG. 7 shows a schematic diagram of an exemplary embodiment of the patient positioning system shown at FIG. 5, in a tilted condition, in one embodiment of the invention.

Further, the motion of the patient support table 125 in the fifth direction is achieved by moving one of the two screw drive assemblies 520 and 525 (as opposed to the motion of the patient support table 125 in the fourth direction achieved by engaging both the screw drive assemblies 520 and 525) subsequent to completing the motion of the patient support table 125 in the fourth direction. One of the coupling devices 450 and 465 can be engaged leaving the other disengaged depending on the side of the inclination desired. If a predetermined standard angular position is desired, the patient support table 125 can be programmed in such a way that the patient support table 125 moves in the vertical direction to a calculated height and subsequently performs the tilt motion.

In one embodiment, the motion of the patient support table 125 along multiple axes (X, Y, Z, R and A) can be achieved by performing one of an automatic and a manual operation. The automatic operation is recommended for emergency purposes and the manual operation for regular use. Further, the motion of the patient support table 125 in each of the five directions (X, Y, R, Z and A) can be achieved with a typical jog, fine and coarse mode mechanisms.

Figure 8:
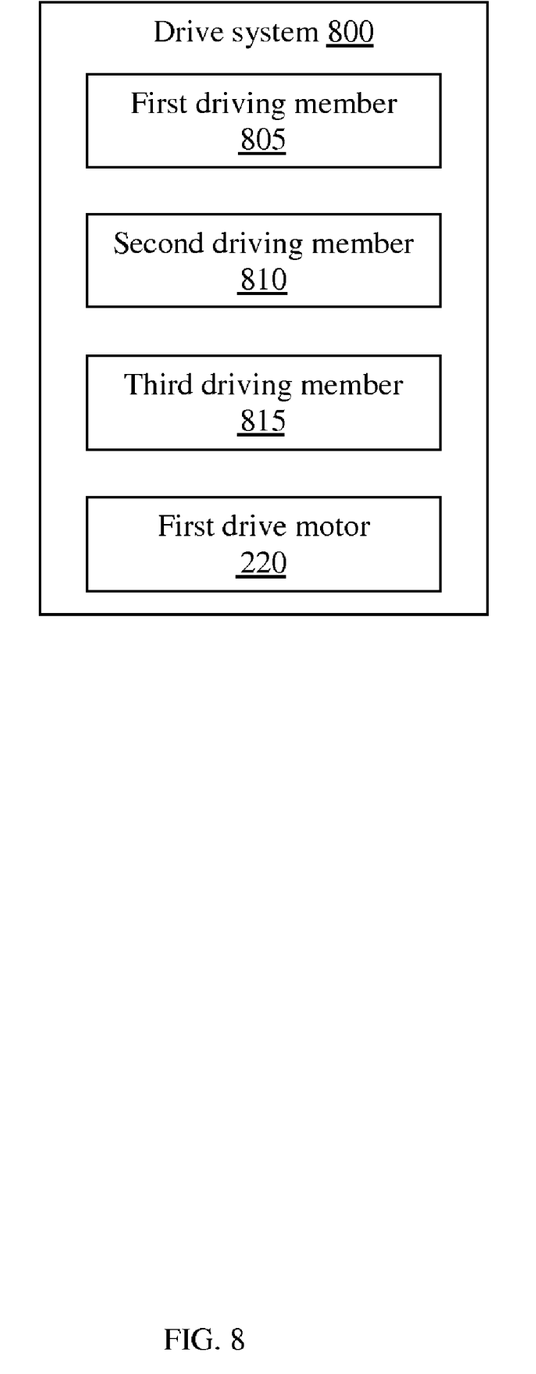
FIG. 8 shows a block diagram of an example of a drive system in an embodiment of the invention.

In another embodiment, a drive system 800 for the patient positioning system 120 is provided as shown in FIG. 8. The drive system 800 comprises at least three driving members namely a first driving member 805, a second driving member 810 and a third driving member 815 configured for moving the patient support table 125 and the first drive motor 220 coupled to the at least three driving members 805, 810 and 815, the first drive motor 220 being configured to drive the at least three driving members 805, 810 and 815.

Figure 9:
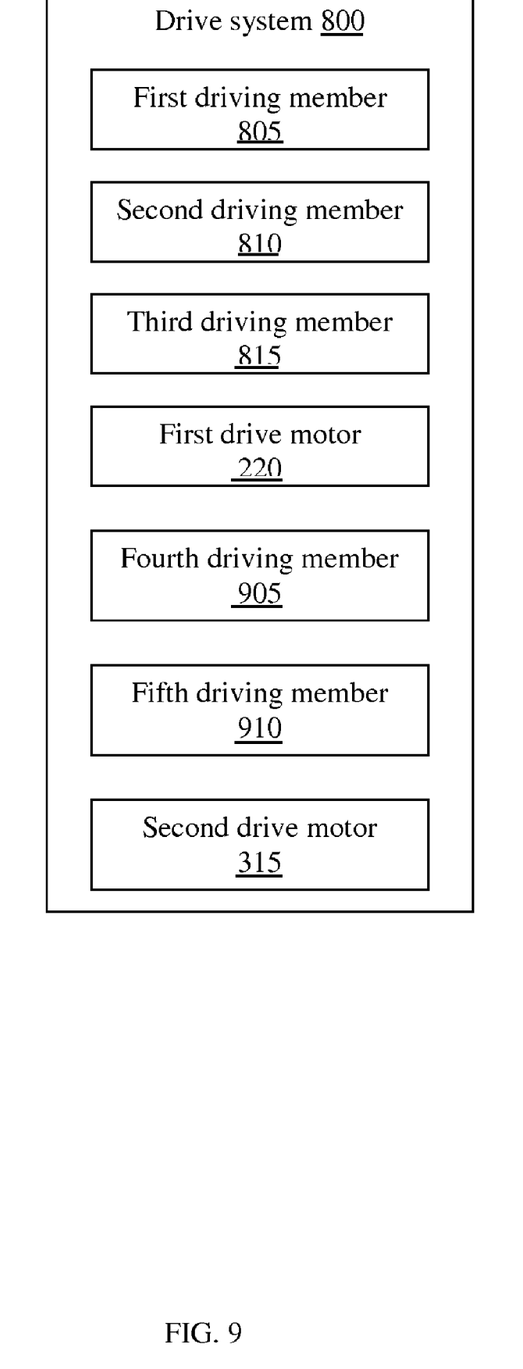
FIG. 9 shows another block diagram of an example of the drive system in another embodiment of the invention.

In another embodiment as shown in FIG. 9, the drive system 800 may further comprise a fourth driving member 905, a fifth driving member 910 and the second drive motor 315. Further, the second drive motor 315 can be configured to drive the fourth driving member 905 and the fifth driving member 910.

In an exemplary embodiment, each of the first driving member 805, the fourth driving member 905 and the fifth driving member 910 may comprise a screw drive assembly 505, 520 and 525 respectively, the second driving member 810 may comprise a rack and pinion drive assembly 510 and the third driving member 815 may comprise a gearbox drive assembly 515.

Skilled artisans shall however appreciate that the number of the driving members is not restricted and the drive system 800 can comprise a number of driving members, the number ranging from three to any number. Accordingly, with the increase in the number of the driving members, the rating of the first drive motor 220 configured to drive the driving members can increase.

Figure 10:
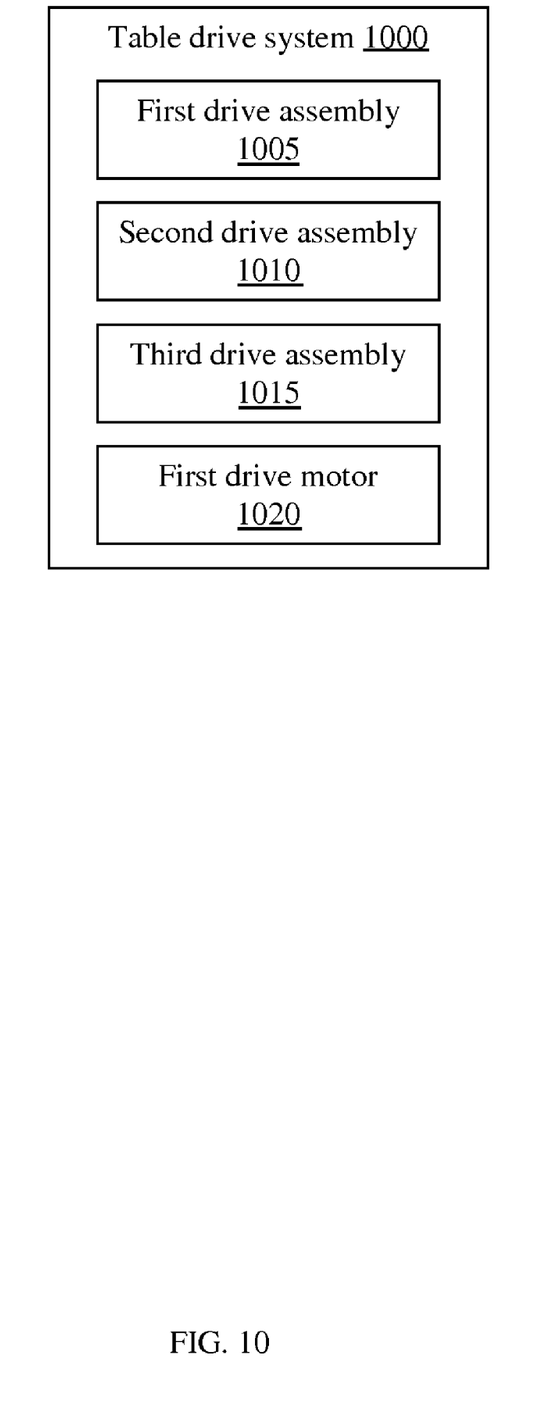
FIG. 10 shows a block diagram of an example of a table drive system in an embodiment of the invention.

In yet another embodiment as shown in FIG. 10, a table drive system 1000 comprising a first drive assembly 1005, similar to the first drive assembly 205 described above, adapted for moving a support table (not shown) in a first direction, a second drive assembly 1010, similar to the second drive assembly 210 described above, adapted for moving the support table (not shown) in a second direction, a third drive assembly 1015, similar to the first drive assembly 215 described above, adapted for moving a support table (not shown) in a third direction and a first drive motor 1020, similar to the first drive motor 220 described above, coupled to the first drive assembly 1005, the second drive assembly 1010 and the third drive assembly 1015 is provided. The first drive motor 1020 can be configured to drive the first drive assembly 1005, the second drive assembly 1010 and the third drive assembly 1015.

Figure 11:
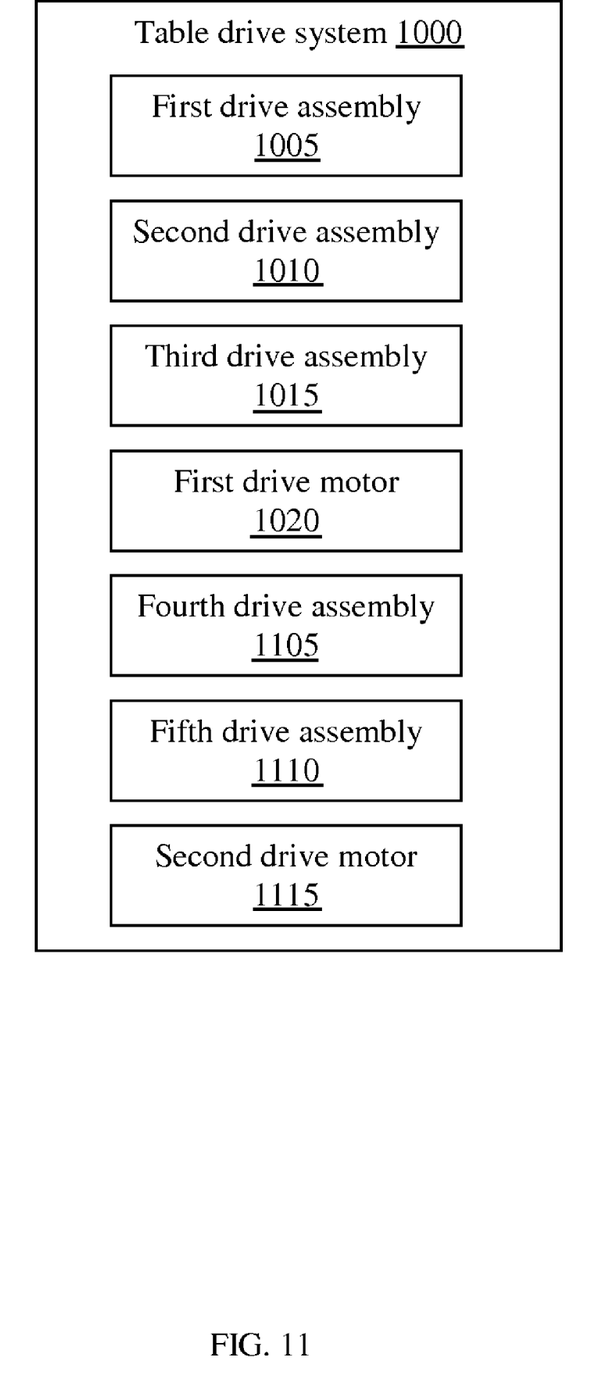
FIG. 11 shows another block diagram of an example of the table drive system in another embodiment of the invention.

In another embodiment, as depicted in FIG. 11, the table drive system 1000 may further comprise a fourth drive assembly 1105 adapted for moving the support table (not shown) in a fourth direction, a fifth drive assembly 1110 adapted for moving the support table (not shown) in a fifth direction and a second drive motor 1115 coupled to the fourth drive assembly 1105 and the fifth drive assembly 1110. Further, the second drive motor 1115 can be configured to drive the fourth drive assembly 1105 and the fifth drive assembly 1110.

Each of the first drive assembly 1005, the second drive assembly 1010, the third drive assembly 1015, the fourth drive assembly 1105 and the fifth drive assembly 1110 of the table drive system 1000 may further comprise a coupling device, a brake device and a feedback device using which the drive assemblies 1005, 1010, 1015, 1105 and 1110 can be coupled to one of the first drive motor 1020 and the second drive motor 1115. The coupling device provides a selective transmission system, the feedback device provides a greater positioning accuracy whereas the brake device provides a better safety and imparts a robust design feature to the table drive system 1000.

The invention provides a simple, compact, reliable, serviceable and accurate patient positioning system 120 comprising two drive motors 220 and 315 for driving multiple drive assemblies 205, 210, 215, 305 and 310. This eliminates the use of multiple drive motors and facilitates cost effectiveness.

The drive system 800 comprising the two drive motor 220 and 315 facilitates optimum utilization of the drive motors 220 and 315 in terms of functioning and idle time.

The necessity of using multiple drive motors is eliminated thereby reducing the number of components utilized in the drive system 800. The reduced number of components leads to improvement in assemble time, increased space for convenience in assembling other parts and lower weight of the drive system 800. As a result of this, the patient positioning system 120 can be sleek with better aesthetics. Reducing the number of components can further help in enhancing the reliability of the patient positioning system 120.

In various embodiments of the invention, a drive system for a patient positioning system and a patient positioning system using a drive system are described. However, the embodiments are not limited and may be implemented in connection with different applications. The application of the invention can be extended to other areas, for example positioning devices. The invention provides a broad concept of using a single drive motor to drive multiple drive assemblies, which can be adapted in a similar positioning system. The design can be carried further and implemented in various forms and specifications.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A table drive system, comprising:
   a first drive assembly configured to move a support table in a first direction;
   a second drive assembly configured to move the support table in a second direction;
   a third drive assembly configured to move the support table in a third direction; and
   a first drive motor coupled to the first drive assembly, the second drive assembly and the third drive assembly, wherein the first drive motor is configured to drive the first drive assembly, the second drive assembly and the third drive assembly.

2. The table drive system of claim 1, further comprising:
   a fourth drive assembly configured to move the support table in a fourth direction;
   a fifth drive assembly configured to move the support table in a fifth direction; and
   a second drive motor coupled to the fourth drive assembly and the fifth drive assembly, wherein the second drive motor is configured to drive the fourth drive assembly and the fifth drive assembly.

3. The table drive system of claim 2, wherein the first direction comprises a longitudinal direction, the second direction comprises a lateral direction, the third direction comprises a rotational direction, the fourth direction comprises a vertical direction and the fifth direction comprises a tilt direction.

4. The table drive system of claim 2, wherein the first drive assembly, the fourth drive assembly and the fifth drive assembly comprise a screw drive assembly.

5. The table drive system of claim 2, wherein the second drive assembly comprises a rack and pinion drive assembly.

6. The table drive system of claim 2, wherein the third drive assembly comprises a gearbox drive assembly.

7. The table drive system of claim 2, further comprising:
   a plurality of coupling devices, wherein each coupling device is coupled to one of the first drive motor and the second drive motor at a first end and one of the first drive assembly, the second drive assembly, the third drive assembly, the fourth drive assembly and the fifth drive assembly at a second end.

8. The table drive system of claim 2, further comprising:
a plurality of brake devices, wherein each brake device is coupled to one of the first drive assembly, the second drive assembly, the third drive assembly, the fourth drive assembly and the fifth drive assembly.

9. The table drive system of claim 2, further comprising:
a plurality of feedback devices, wherein each feedback device is coupled to one of the first drive assembly, the second drive assembly, the third drive assembly, the fourth drive assembly and the fifth drive assembly.

10. The table drive system of claim 9, wherein each feedback device is an absolute encoder.

11. A drive system for a patient positioning system, the drive system comprising:
at least three driving members configured to move a patient support table; and
a first drive motor coupled to the at least three driving members, wherein the first drive motor is configured to drive the at least three driving members.

12. The drive system of claim 11, wherein a first of the at least three driving members comprises a screw drive assembly.

13. The drive system of claim 11, wherein a second of the at least three driving members comprises a rack and pinion drive assembly.

14. The drive system of claim 11, wherein a third of the at least three driving members comprises a gearbox drive assembly.

15. The drive system of claim 11, further comprises:
a fourth driving member;
a fifth driving member; and
a second drive motor coupled to the fourth driving member and the fifth driving member, wherein the second drive motor is configured to drive the fourth driving member and the fifth driving member.

16. The drive system of claim 15, wherein the fourth driving member and the fifth driving member comprise a screw drive assembly.

17. A patient positioning system comprising:
a patient support table;
a first drive assembly adapted to move the patient support table in a first direction;
a second drive assembly adapted to move the patient support table in a second direction;
a third drive assembly adapted to move the patient support table in a third direction; and
a first drive motor in combination with the first drive assembly, the second drive assembly and the third drive assembly, wherein the first drive motor is configured to drive the first drive assembly, the second drive assembly and the third drive assembly.

18. The patient positioning system of claim 17, further comprising:
a fourth drive assembly adapted to move the patient support table in a fourth direction;
a fifth drive assembly adapted to move the patient support table in a fifth direction; and
a second drive motor coupled to the fourth drive assembly and the fifth drive assembly, wherein the second drive motor is configured to drive the fourth drive assembly and the fifth drive assembly.

19. The patient positioning system of claim 18, wherein the first drive assembly is adapted to move the patient support table along a longitudinal axis, the second drive assembly is adapted to move the patient support table along a lateral axis, the third drive assembly is adapted to move the patient support table along a rotational axis, the fourth drive assembly is adapted to move the patient support table along a vertical axis and the fifth drive assembly is adapted to move the patient support table along a tilt axis.

20. The patient positioning system of claim 18, wherein the first drive assembly, the fourth drive assembly and the fifth drive assemblies comprise a screw drive assembly.

21. The patient positioning system of claim 18, wherein the second drive assembly comprises a rack and pinion drive assembly.

22. The patient positioning system of claim 18, wherein the third drive assembly comprises a gearbox drive assembly.

* * * * *